(12) United States Patent
Norton et al.

(10) Patent No.: US 9,101,373 B2
(45) Date of Patent: Aug. 11, 2015

(54) SELF-CENTERING DRILL GUIDE

(71) Applicant: Biomet Sports Medicine, LLC, Warsaw, IN (US)

(72) Inventors: Daniel Norton, Winona Lake, IN (US); Kevin T. Stone, Winona Lake, IN (US); Gregory J. Denham, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 358 days.

(21) Appl. No.: 13/651,986

(22) Filed: Oct. 15, 2012

(65) Prior Publication Data

US 2014/0107657 A1 Apr. 17, 2014

(51) Int. Cl.
*A61B 17/17* (2006.01)
*A61B 17/88* (2006.01)
*A61B 17/90* (2006.01)
*A61B 17/16* (2006.01)
*A61B 17/04* (2006.01)

(52) U.S. Cl.
CPC ......... *A61B 17/1796* (2013.01); *A61B 17/0401* (2013.01); *A61B 17/17* (2013.01); *A61B 17/88* (2013.01); *A61B 17/1631* (2013.01); *A61B 2017/0408* (2013.01); *A61B 2017/0409* (2013.01); *A61B 2017/0445* (2013.01); *A61B 2017/90* (2013.01)

(58) Field of Classification Search
CPC .................. A61B 2017/0409; A61B 17/1631; A61B 17/17; A61B 17/1796; A61B 17/88; A61B 2017/90
USPC ....... 408/72 B, 115 B, 115 R, 127; 606/86 R, 606/96–98, 104
See application file for complete search history.

(56) References Cited

U.S. PATENT DOCUMENTS

| | | | |
|---|---|---|---|
| 5,254,130 A | 10/1993 | Poncet et al. | |
| 5,318,528 A | 6/1994 | Heaven et al. | |
| 5,330,468 A | 7/1994 | Burkhart | |
| 5,522,788 A | 6/1996 | Kuzmak | |
| 5,522,844 A * | 6/1996 | Johnson | 606/232 |
| 5,607,432 A * | 3/1997 | Fucci | 606/104 |
| 5,766,196 A | 6/1998 | Griffiths | |
| 5,904,685 A * | 5/1999 | Walawalkar | 606/916 |
| 6,358,251 B1 | 3/2002 | Mirza | |
| 6,419,678 B1 * | 7/2002 | Asfora | 606/96 |
| 6,875,219 B2 | 4/2005 | Arramon et al. | |
| 7,044,934 B2 | 5/2006 | Mickley | |
| 7,201,722 B2 | 4/2007 | Krueger | |
| 7,611,521 B2 | 11/2009 | Lubbers et al. | |
| 8,608,777 B2 * | 12/2013 | Kaiser et al. | 606/232 |
| 2008/0091217 A1 | 4/2008 | Dross | |
| 2008/0188854 A1 * | 8/2008 | Moser | 606/80 |
| 2009/0192545 A1 | 7/2009 | Workman | |
| 2010/0076502 A1 * | 3/2010 | Guyer et al. | 606/86 R |
| 2012/0245586 A1 * | 9/2012 | Lehenkari et al. | 606/80 |
| 2013/0261628 A1 * | 10/2013 | Burley et al. | 606/80 |

* cited by examiner

*Primary Examiner* — Larry E Waggle, Jr.
(74) *Attorney, Agent, or Firm* — Schwegman Lundberg & Woessner, P.A.

(57) ABSTRACT

A drill guide including an inner surface, a tip, and a deflecting device. The inner surface defines a bore extending through the drill guide. The bore is configured to individually receive therein a flexible drill bit and an insertion tool with a suture anchor mounted thereto. The tip is at a distal end of the bore and defines a tip aperture of the bore. The deflecting device is proximal to the tip and includes at least one bearing surface configured to deflect the drill bit within the bore.

22 Claims, 8 Drawing Sheets

SELF-CENTERING DRILL GUIDE

FIELD

The present disclosure relates to a self-centering drill guide.

BACKGROUND

This section provides background information related to the present disclosure which is not necessarily prior art.

A drill guide can be used by a surgeon to direct a drill bit to bone at a surgical site. The drill bit can be inserted through a bore defined by the guide, and then rotated with a drill to form a bone hole at the site. A suture anchor can be inserted through the bore of the same drill guide using an insertion tool, and implanted in the bone hole in order to, for example, anchor tissue at the surgical site. The guide need not be moved after the bone hole is formed, and thus insertion of the anchor in the bone hole is facilitated and made more accurate because the guide is already aligned with the hole.

The drill bit often has an outer diameter that is smaller than an outer diameter or width of the anchor. To accommodate the anchor, the bore of the guide has an inner diameter that is greater than the outer diameter of the drill bit, which may not be optimal for drilling. Because the diameter of the bore is greater than the outer diameter of the drill bit, the guide will not be able to fully constrain the drill bit, which may result in the bone hole being drilled off-center from the guide. The guide thus may not accurately align with the bone hole, which may result in the anchor being damaged during insertion or missing the hole completely. This issue is exacerbated when the guide tube is curved because the drill may be angled away from the bend and press against an edge of the guide, which may damage the drill bit and/or make it difficult to form the bone hole exactly at an intended location.

SUMMARY

This section provides a general summary of the disclosure, and is not a comprehensive disclosure of its full scope or all of its features.

The present teachings provide for a drill guide including an inner surface, a tip, and a deflecting device. The inner surface defines a bore extending through the drill guide. The bore is configured to individually receive therein a flexible drill bit and an insertion tool with a suture anchor mounted thereto. The tip is at a distal end of the bore and defines a tip aperture of the bore. The deflecting device is proximal to the tip and includes at least one deflecting surface configured to deflect the drill bit within the bore.

The present teachings also provide for a drill guide including a curved portion, a tip, a deflection device, and at least one slot defined by the deflection device. The curved portion includes an inner surface defining a bore extending through the curved portion. The bore is configured to individually receive therein a drill bit and an insertion tool. The tip of the curved portion is at a distal end of the curved portion. The tip defines a tip aperture of the bore. The deflection device of the inner surface is proximal to the tip. The deflection device defines a first dimension of the bore sized and configured to deflect the drill bit and the insertion tool within the bore.

The present teachings further provide for a method of forming a bone hole in bone and implanting a suture anchor therein. The method includes the following: positioning a drill guide against an outer surface of the bone at a first location; inserting a drill bit in a bore defined by the drill guide such that a tip of the drill bit extends out from within the bore through a tip aperture defined by the bore, the drill guide includes a deflection device with at least one deflecting surface configured to center the drill bit within the bore, the deflecting surface defines a first dimension of the bore; drilling the bone hole in the bone with the drill bit; and inserting an insertion device with the suture anchor mounted thereto through the bore and implanting the suture anchor within the bone hole, the suture anchor including a width that is greater than the first dimension, the suture anchor is moved past the deflection device through grooves defined by deflection device, the grooves define a second dimension of the bore that is greater than the first dimension.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figures 1, 2:
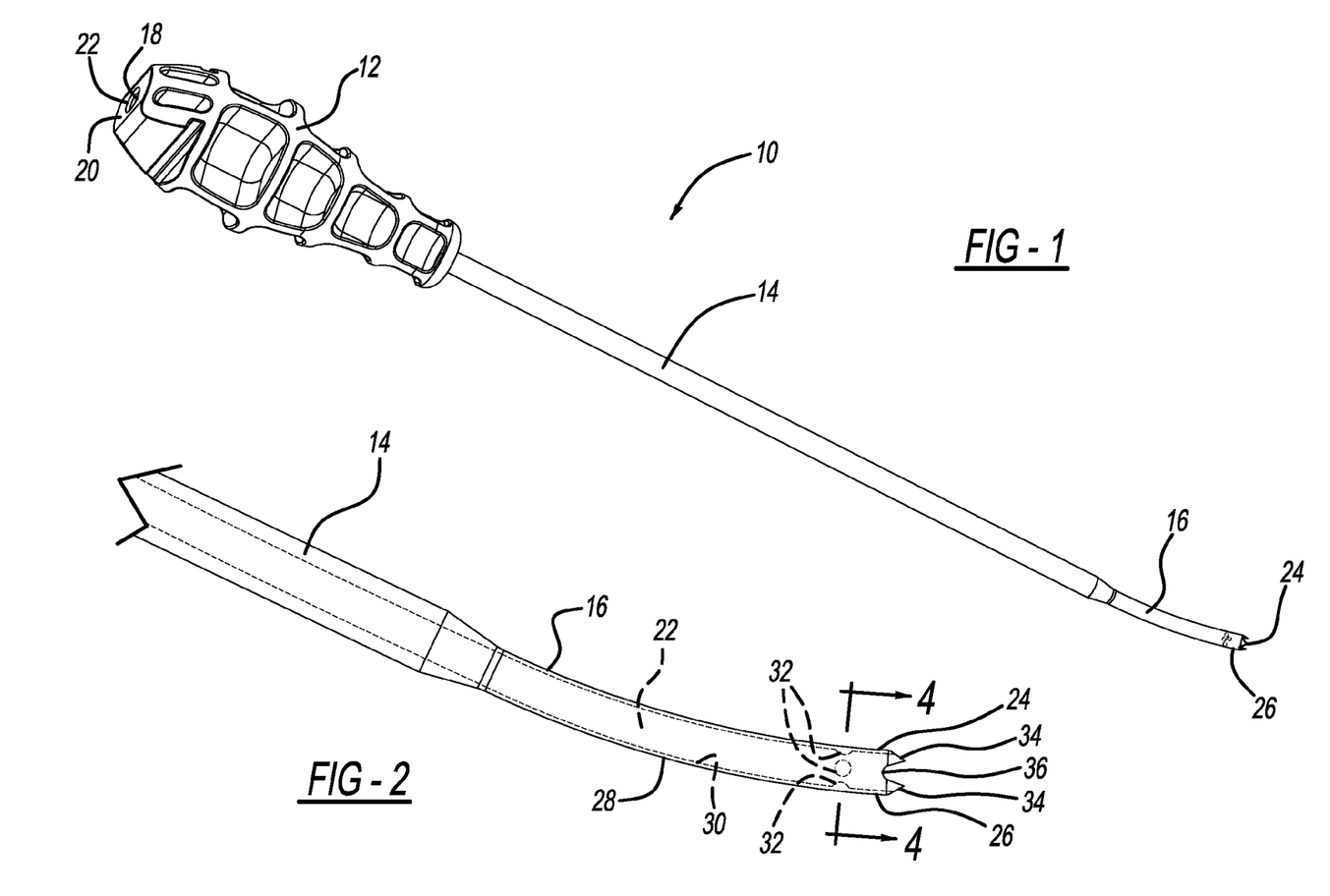
FIG. 1 is a perspective view of a drill guide according to the present teachings.
FIG. 2 is a side view of a curved portion of the drill guide of FIG. 1.

With initial reference to FIG. 1, a drill guide according to the present teachings is illustrated at reference numeral 10. The drill guide 10 generally includes a handle 12, an elongated linear portion 14, and a curved portion 16. The drill guide 10 can be rigid or flexible, and made of any suitable material, such as steel.

The elongated linear portion 14 extends from the handle 12, and the curved portion 16 extends from the elongated linear portion 14 such that the elongated linear portion 14 is between the handle 12 and the curved portion 16. The handle 12 defines a handle aperture 18 at a proximal end 20 of both the handle 12 and the drill guide 10 as a whole. The handle aperture 18 provides access to a bore 22, which is generally defined by the handle 12, the elongated linear portion 14, and the curved portion 16. The bore 22 thus extends through the handle 12, the elongated linear portion 14, and the curved portion 16 to an open tip 24. The tip 24 is at a distal end 26 of both the curved portion 16 and the drill guide 10 as a whole. The drill guide 10 is configured for use with a variety of surgical procedures, such as those that include directing a drill bit to bone and implanting a suture anchor in a hole formed by the drill bit, the suture anchor implanted with an insertion tool inserted through the bore.

With additional reference to FIG. 2, the curved portion 16 generally includes an outer surface 28 and an inner surface 30, which is opposite the outer surface 28. The inner surface 30 extends along a length of the curved portion 16 and defines the bore 22 at the curved portion 16. The outer surface 28 and the inner surface 30 are both generally curved along their length to provide the curved portion 16 with a curved profile.

Proximate to the tip 24, the curved portion 16 further includes a centering device having a plurality of deflecting (or centering) bearings or surfaces 32, which can serve as alignment members. The deflecting surfaces 32 can be any suitable surface, device, or mechanism suitable to provide the bore 22 with a reduced diameter portion proximate to the tip 24 to deflect and/or center a drill bit within the bore 22. As illustrated in FIGS. 1-5, the deflecting surfaces 32 are spaced apart protrusions of the inner surface 30 that extend radially towards a center of the bore 22. Any suitable number of deflecting surfaces 32 can be included, such as the four illustrated in FIGS. 1-5. The deflecting surfaces 32 are evenly spaced radially about the inner surface 30. Opposing deflecting surfaces 32 define a dimension or diameter D1 of the bore 22, which is smaller than the dimension or diameter D2 of the bore 22 at opposing portions of the inner surface 30 between the deflecting surfaces 32. Although the dimensions D1 and D2 of the bore 22 are referred to herein as diameters, all references to diameters generally include transverse dimensions so as to not restrict the bore 22 to any particular shape. Regardless of the shape of the bore 22, the dimension or diameter D1 is smaller than the dimension or diameter D2. This is the case with respect to all of the different centering devices set forth herein.

The deflecting surfaces 32 generally define slots or grooves 38 between neighboring deflecting surfaces 32. The deflecting surfaces 32 can be formed in any suitable manner, such as by stamping or molding. The deflecting surfaces 32 can also be separate components secured to the inner surface 30 in any suitable manner.

Figures 15, 16:
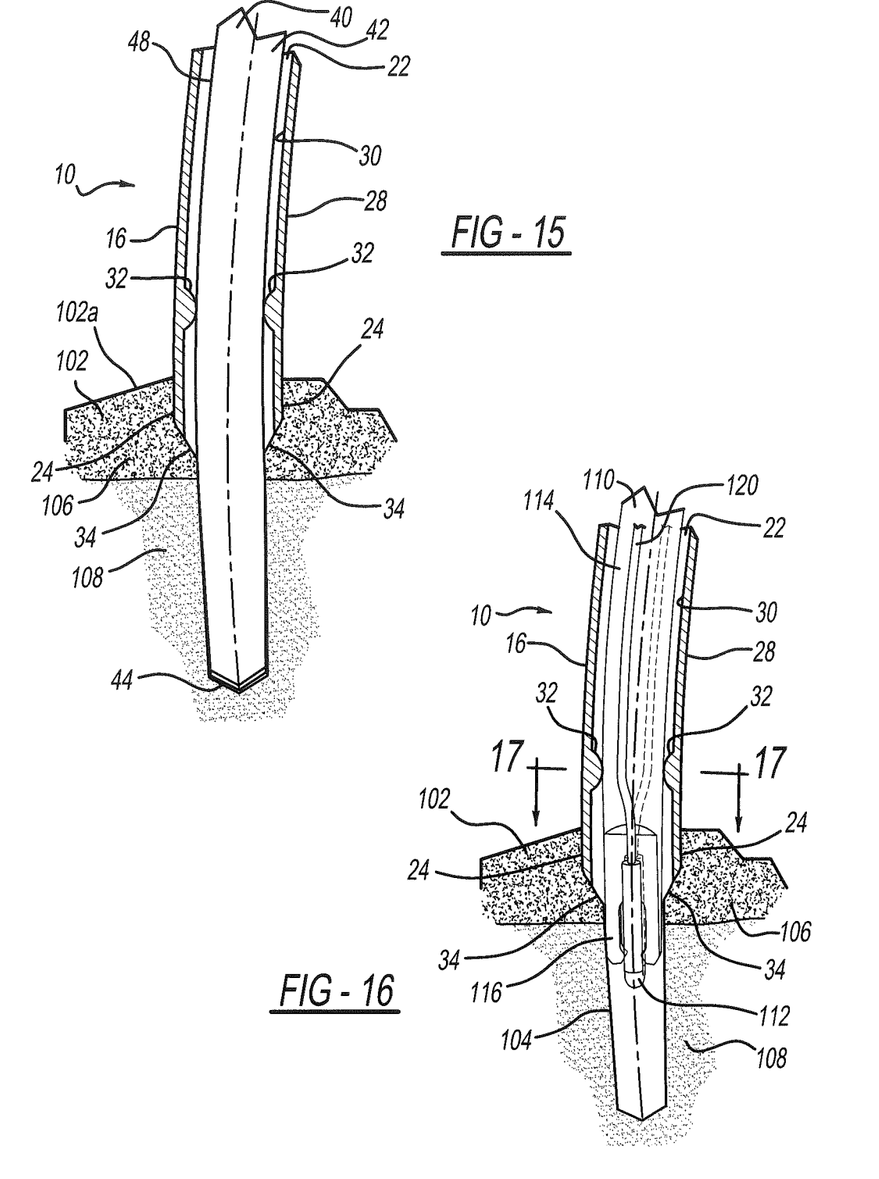
FIG. 15 is a cross-sectional view of the drill guide of FIG. 1 in contact with bone, the drill bit is seated in the bore of the drill guide and is within the bone to form a bone hole.
FIG. 16 is a cross-sectional view of the drill guide of FIG. 1 in contact with the bone, an insertion tool is seated within the bore, a suture anchor is mounted to the insertion tool for implantation in the bone hole.

The tip 24 further includes a plurality of distal teeth 34 that define a tip aperture 36. The teeth 34 facilitate engagement of the curved portion 16 with bone 102 (FIGS. 15, 16, and 18) in order to maintain the tip 24 at a desired position during drilling of a bone hole 104. The tip aperture 36 defines an opening of the bore 22 at the distal end 26.

Figure 4:
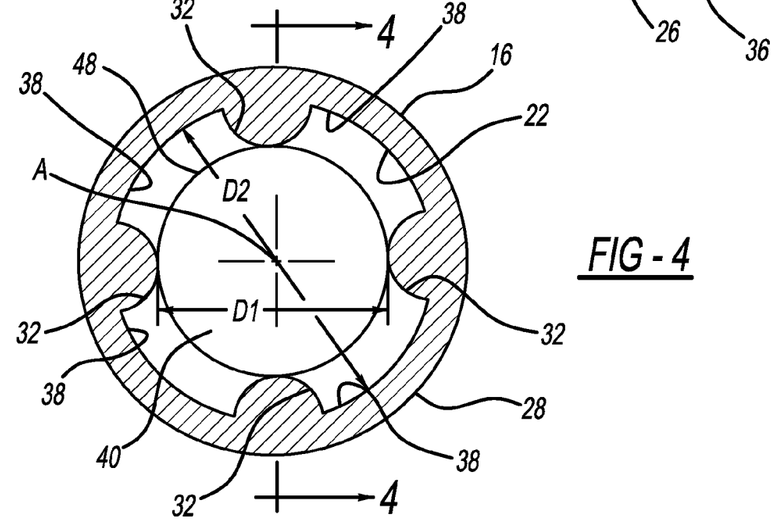
FIG. 4 is a cross-sectional view taken along line 4-4 of FIG. 2 including a drill bit seated in a bore defined by the curved portion.
Figure 5:
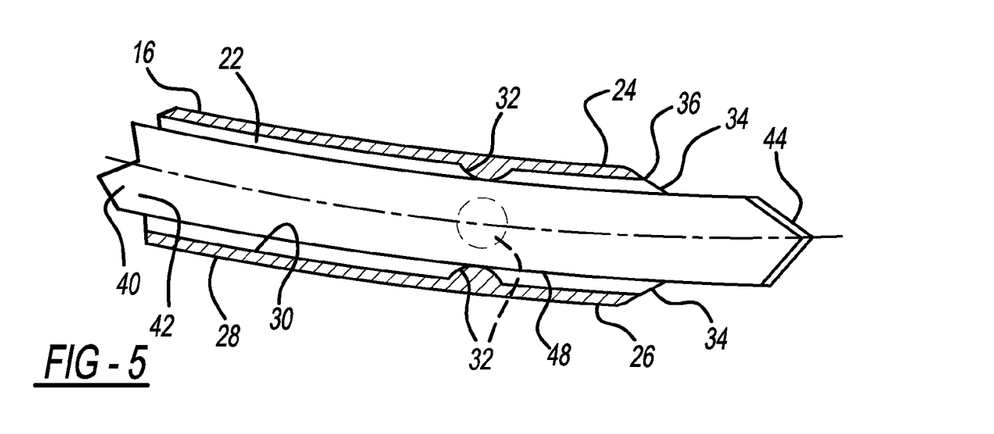
FIG. 5 is a cross-sectional view taken along line 5-5 of FIG. 4.

With reference to FIGS. 4 and 5, a drill bit 40 is illustrated. The drill bit 40 is flexible and generally includes a drill body 42, and a drill bit tip 44. The drill bit tip 44 is generally sharpened sufficient to cut bone. The body 42 includes an outer body surface 48, which generally has a circular cross-section and a diameter that is slightly smaller than D1, such that the outer body surface 48 will closely abut the deflecting surfaces 32, as illustrated in FIG. 4.

During use of the drill guide 10, the drill bit 40 is initially inserted through the handle aperture 18 into the bore 22. The drill bit 40 is passed through the handle 12 and the elongated linear portion 14 and ultimately positioned in the bore 22 at the curved portion 16. The drill bit tip 44 extends out beyond the tip aperture 36 in order to cut bone.

Figure 3:
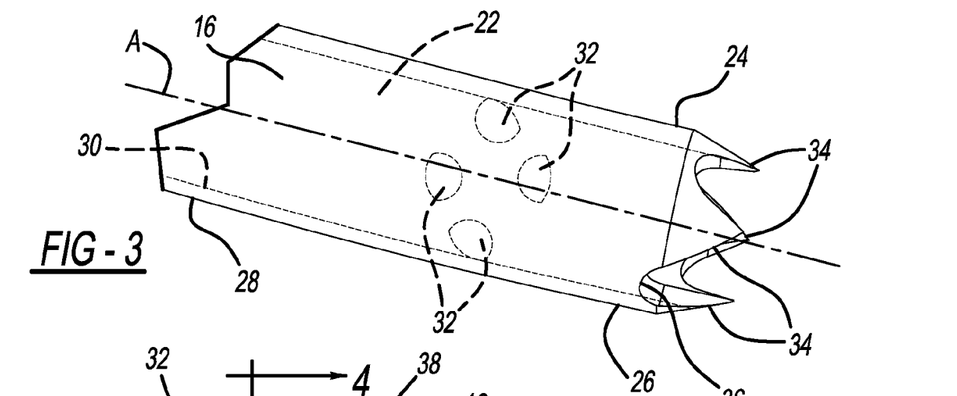
FIG. 3 is a side view of a distal portion of the curved portion.

The outer body surface 48 of the drill bit 40 is sized to abut the deflecting surfaces 32 in order to center the drill bit 40 within the bore 22 at the curved portion 16. As illustrated in FIGS. 3-4, the deflecting surfaces 32 center the drill bit 40 along a longitudinal axis A of the bore 22. Because the centering bearings 32 are proximate to the tip aperture 36, the drill bit 40 is further centered in the tip aperture 36 along the longitudinal axis A so that the drill bit 40 does not contact the inner surface 30 of the curved portion 16, which can prevent damage to the drill bit 40 and the curved portion 16, as well as provide for more accurate center positioning of the drill bit 40. The deflecting surfaces 32 also reduce friction between the outer body surface 48 and the inner surface 30 of the drill guide 10.

Because the deflecting surfaces 32 are spaced apart, gaps or slots 38 are defined therebetween. The slots 38 permit passage of an anchor for example, such as a soft anchor mounted to an insertion tool, as described herein in connection with the description of FIGS. 15-18. Because the diameter D2 of the bore 22 is not reduced at the slots 38 between the deflecting surfaces 32, the width of the soft anchor may be as wide as D2, and thus wider than both D1 and the diameter of the drill bit 40, which is nearly equal to D1. Thus, the deflecting surfaces 32 center the drill bit 40 along the longitudinal axis A and in the tip aperture 36, and permit passage of a suture anchor having a width greater than the diameter D1 of the bore 22 in the reduced diameter portion of the bore 22 where the deflecting surfaces 32 oppose one another.

Figure 5A:
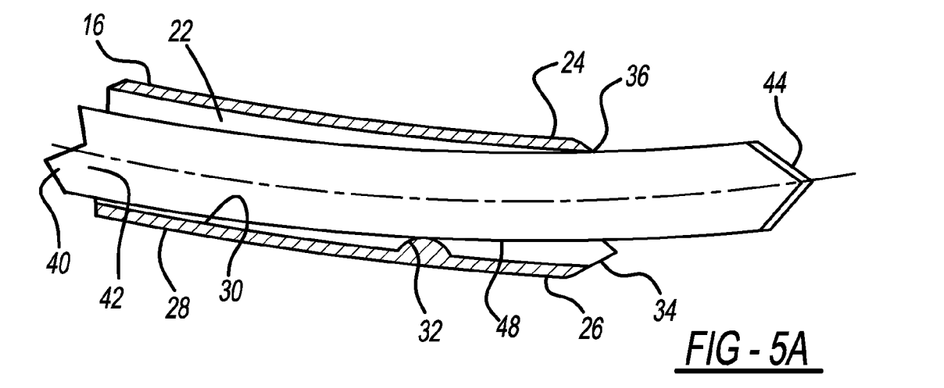
FIG. 5A is a view similar to that of FIG. 5, but with the drill guide modified to include only a single drill bit deflection member.
Figure 5B:
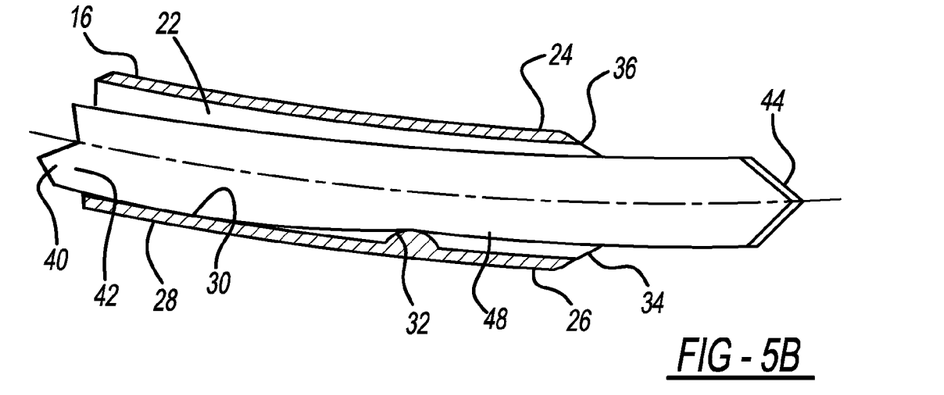
FIG. 5B is similar to FIG. 5A, but illustrates the drill bit contacting both the single drill bit deflection member and an inner surface of the drill guide.

As illustrated in FIG. 5A, the drill bit 40 need not be centered in the tip aperture 36. The curved portion 16 of the drill guide 10 illustrated in the FIG. 5A includes a single deflecting surface 32, which causes the drill bit 40 to not be centered in the tip aperture 36. FIG. 5B is similar to FIG. 5A, but the drill bit 40 contacts and deflects off of the inner surface 30 of the curved portion 16 of the drill guide 10 and then is deflected by deflecting surface 32, which centers the drill bit 40 in the tip aperture 36. The deflecting surfaces 32 thus help guide the drill bit 40 through the bore 22 and prevent the drill bit 40 from becoming wedged or stuck within the bore 22.

Figure 5C:
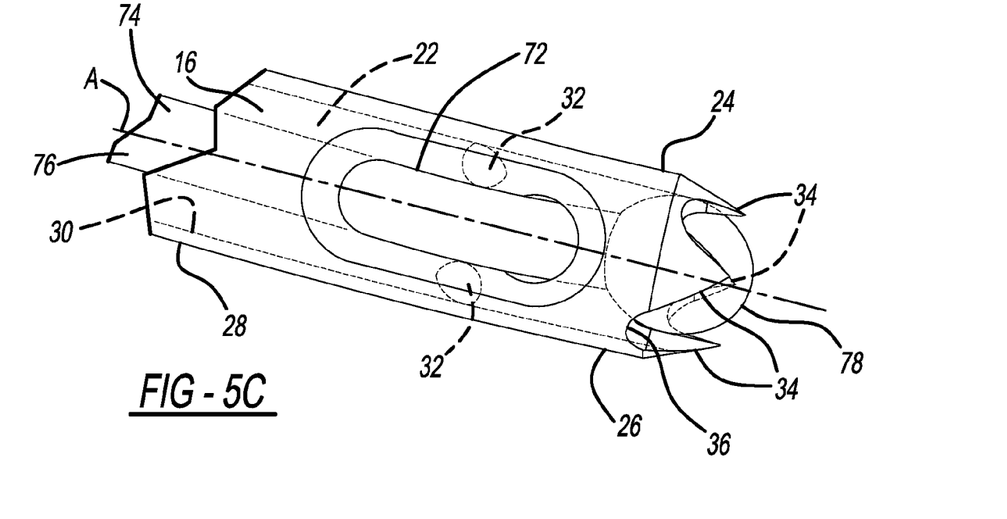
FIG. 5C is a perspective view of the distal portion of the curved portion of the drill guide of FIG. 1 modified to include an obturator slot to accommodate insertion of an obturator within the drill guide.

FIG. 5C illustrates the curved portion 16 defining a side through slot 72 proximate to the tip aperture 36, and an obturator 74. The obturator 74 includes a shaft 76 and a head 78. The shaft 76 is generally circular in cross-section and has an outer diameter that is less than the diameter D2 of the bore 22. The head 78 is generally spherical and defines an outer diameter that at its greatest width is slightly smaller than the diameter D2 of the bore 22, but is greater than the diameter D1 of the bore 22. During insertion of the drill guide 10 through tissue, the obturator 74 is inserted within the bore 22 to prevent tissue and other materials from entering and clogging the bore 22. The obturator 74 is positioned such that the shaft 76 extends from the tip 24 through the curved portion 16, the elongated linear portion 14, and the handle 12. The shaft 76 extends from the handle 12 to permit the obturator 74 to be grasped by a surgeon. The head 78 is positioned at the tip 24 of the drill guide 10 such that the head 78 of the obturator 74 slightly extends distally beyond the teeth 34.

The obturator 74 is inserted within the bore 22 by inserting the head 78 first through the handle 12, and then through the elongated linear portion 14 to the curved portion 16 and ultimately to the tip 24. Upon contacting the deflecting surfaces 32, the head 78 deflects partially out from within the bore 22 through the slot 72. After passing over the deflecting surfaces 32, the head 78 retreats back to being entirely within the bore 22. The slot 72 thus accommodates the head 78 and provides a clearance for the head 78 as the head 78 passes over the deflecting surfaces 32 due to the greatest outer diameter of the head 78 being greater than the diameter D1 of the bore 22 at the deflecting surfaces 32.

Figure 6:
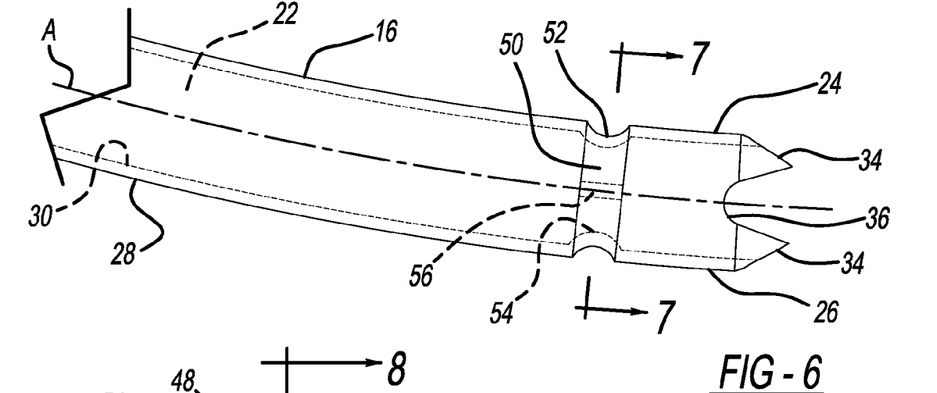
FIG. 6 is a side view of another curved portion of the drill guide according to the present teachings.
Figure 7:
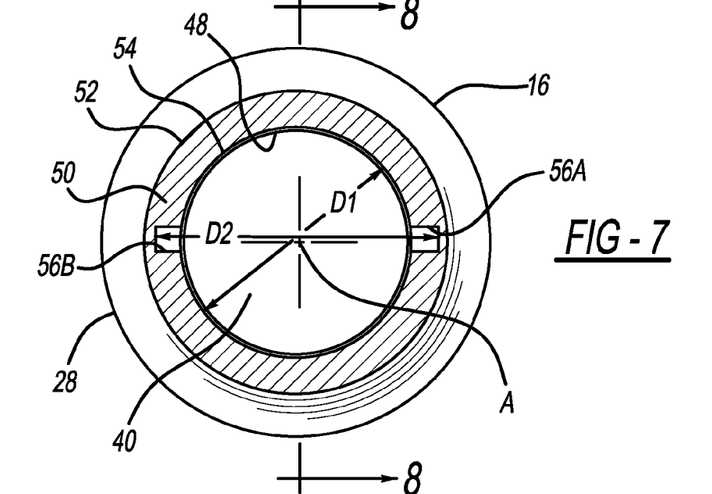
FIG. 7 is a cross-sectional view taken along line 7-7 of FIG. 6 including the drill bit seated in the bore defined by the curved portion.
Figure 8:
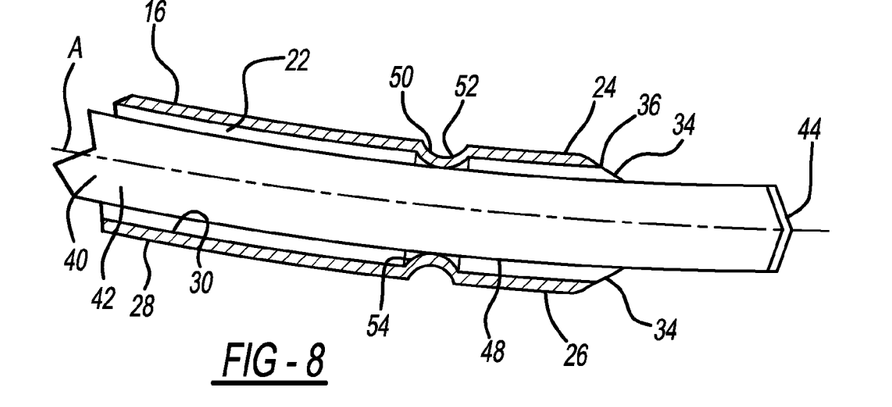
FIG. 8 is a cross-sectional view taken along line 8-8 of FIG. 7.

With additional reference to FIGS. 6-8, instead of the deflecting surfaces 32, the centering device can include a centering bearing surface in the form of an annular ring 50. The annular ring 50 is generally arranged proximate to the distal end 26 and the tip aperture 36, and is arranged in a position similar to that of the deflecting surfaces 32. The annular ring 50 generally includes an outer surface 52 and an inner surface 54. The outer surface 52 is generally a portion of the outer surface 28 of the curved portion 16, which is recessed beneath the remainder of the outer surface 28. The outer surface 52 of the annular ring 50 extends about an outer circumference of the curved portion 16. The inner surface 54 of the annular ring 50 is generally a portion of the inner surface 30 of the curved portion 16 that provides the bore 22 with a diameter D1 that is smaller than the diameter of the bore 22 provided by the remainder of the inner surface 30. The inner surface 54 therefore generally provides the bore 22 with decreased diameter portion D1 at the inner surface 54, and as illustrated in FIGS. 7 and 8. The inner surface 54 is sized to contact the outer body surface 48 of the drill bit 40 to center the drill bit 40 within the bore 22 and the tip aperture 36 along the longitudinal axis A extending through the center of the bore 22 and provide a bearing surface for the drill bit 40. The annular ring 50 can be formed in any suitable manner, such as by crimping.

As illustrated in FIG. 7, the annular ring 50 defines a first slot 56A and a second slot 56B, which oppose one another at the inner surface 54. The first slot 56A and the second slot 56B are generally defined in the inner surface 54 to provide the annular ring 50 with an increased diameter D2 at the inner surface 54 that provides a clearance across the annular ring 50 and is approximately equal to a diameter of the remainder of the bore 22 at the inner surface 30 of the curved portion 16.

The slots 56A and 56B are sized and configured to permit passage of a suture anchor mounted to an insertion device, such as a suture anchor having a width greater than the diameter D1.

Figure 9:
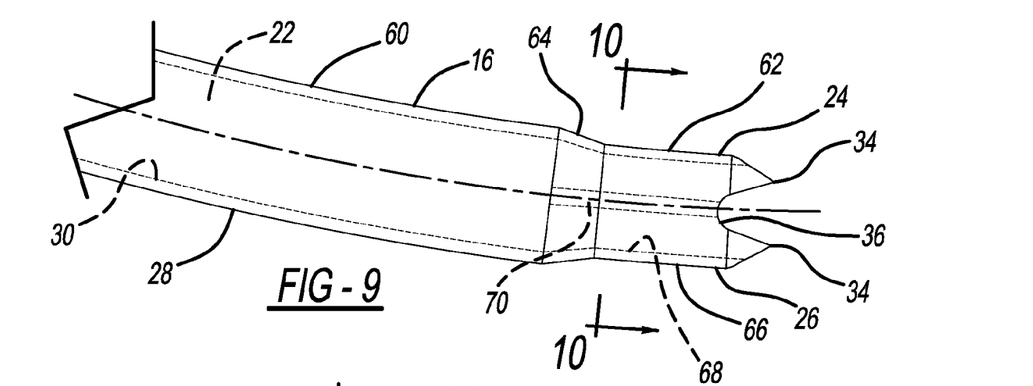
FIG. 9 is a side view of an additional curved portion of the drill guide according to the present teachings.
Figure 10:
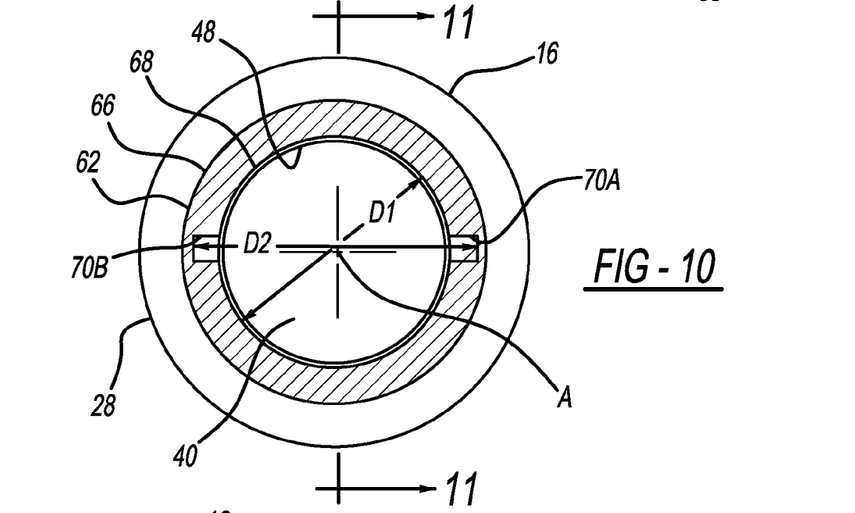
FIG. 10 is a cross-sectional view taken along line 10-10 of FIG. 9 including the drill bit seated in the bore defined by the curved portion.
Figure 11:
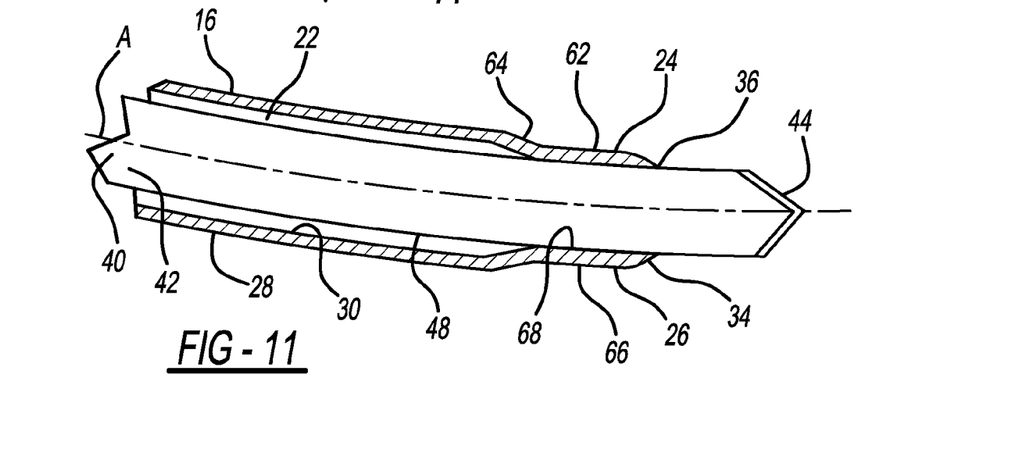
FIG. 11 is a cross-sectional view taken along line 11-11 of FIG. 10.

With additional reference to FIGS. 9-11, the curved portion 16 can include a first diameter portion 60, a second diameter portion 62, and a tapered neck portion 64 between the first diameter portion 60 and the second diameter portion 62. The second diameter portion 62 is at the distal end 26 of the drill guide 10 and thus includes the tip 24 and the teeth 34. The second diameter portion 62 generally includes an outer surface 66 and an inner surface 68 that is opposite to the outer surface 66. The inner surface 68 defines the bore 22 within the second diameter portion 62. The inner surface 68 provides the bore 22 with a smaller diameter at the second diameter portion 62 as compared to the diameter D1 of the bore 22 at the first diameter portion 60. The second diameter portion 62 can be formed in any suitable manner, such as by swaging the curved portion 16 at the distal end 26 of the drill guide 10.

With additional reference to FIGS. 10 and 11, the diameter D1 of the bore 22 at the second diameter portion 62 is sized to abut the outer body surface 48 of the drill bit 40, and thus the inner surface 68 provides a centering device for centering the drill bit 40 along the longitudinal axis A that extends along the center of the bore 22. The second diameter portion 62 also provides a centering bearing surface for the drill bit 40. As illustrated in FIG. 10, the second diameter portion 62 includes a first slot 70A and second slot 70B defined within the inner surface 68. The first slot 70A is opposite to the second slot 70B. The first and second slots 70A and 70B define diameter D2 of the bore 22 therebetween, which accommodate passage of a suture anchor having a width that is wider than the diameter D1 of the bore 22 at the second diameter portion 62 and greater than the diameter of the drill body 42. The first and the second slots 70A and 70B thus define a clearance region for the suture anchor.

Figure 12:
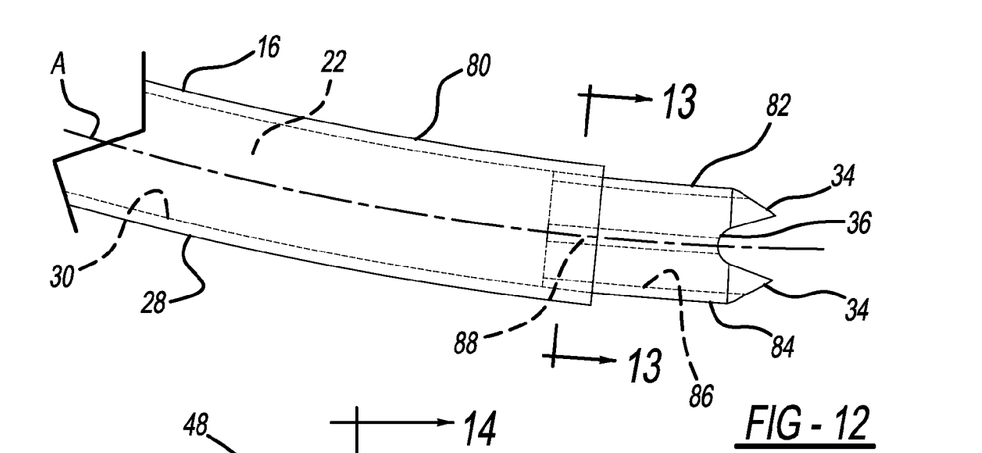
FIG. 12 is an additional curved portion of the drill guide according to the present teachings.
Figure 13:
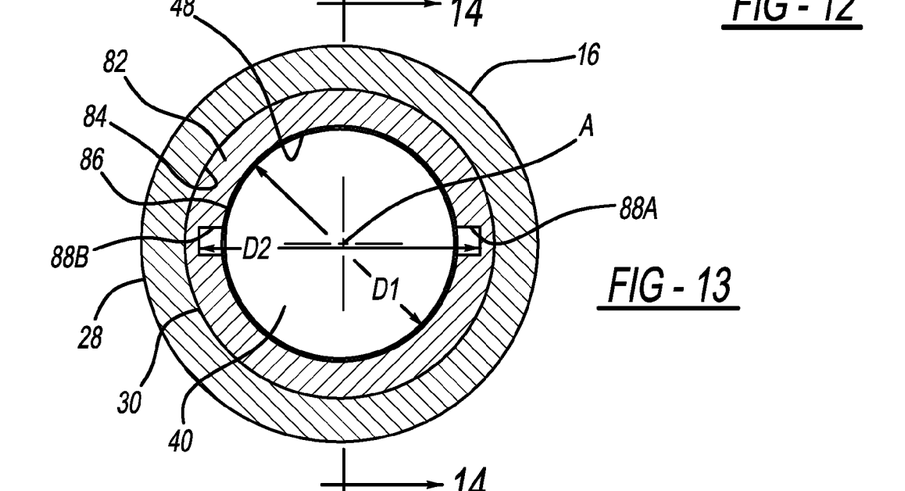
FIG. 13 is a cross-sectional view taken along line 13-13 of FIG. 12 including the drill bit seated in the bore defined by the curved portion.
Figure 14:
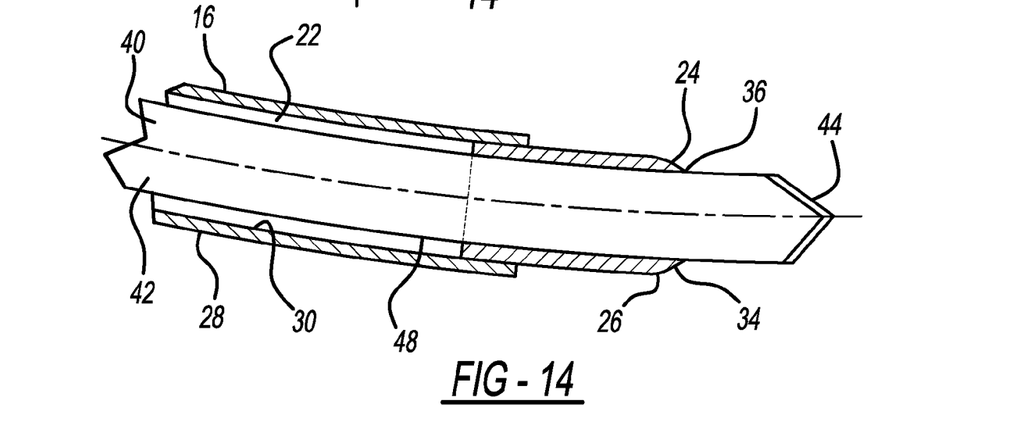
FIG. 14 is a cross-sectional view taken along line 14-14 of FIG. 13.

With additional reference to FIGS. 12-14, the curved portion 16 can include a first portion 80 and a second portion 82, which is fastened to the first portion 80. The first portion 80 includes the outer surface 28 and the inner surface 30 of the bore 22. The second portion 82 includes an outer surface 84 and an inner surface 86 that is opposite to the outer surface 84. The outer surface 84 has a circumference that is smaller than a circumference of the outer surface 28. The inner surface 86 defines the bore 22 with a diameter D1 that is smaller than the diameter of the bore 22 defined by the inner surface 30 at the first portion 80. Therefore, the bore 22 has a smaller diameter in the second portion 82 as compared to the first portion 80. The second portion 82 can be fastened to the first portion 80 in any suitable manner, such as by welding the outer surface 84 to the inner surface 30.

As illustrated in FIGS. 13-14, the inner surface 86 defines diameter D1 of the bore 22 that is just slightly larger than the outer body surface 48 of the drill bit 40 so as to contact the outer body surface 48 and center the drill bit 40, within the second portion 82 and the tip aperture 36 along the longitudinal axis A extending along a center of the bore 22. Therefore, the second portion 82, and particularly the inner surface 86 of the second portion 82, provides a centering device for centering the drill bit 40 and a bearing surface for the drill bit 40.

The second portion 82 defines a first slot 88A and a second slot 88B at the inner surface 86. The first slot 88A is arranged spaced apart from and opposite to the second slot 88B. The slots 88A and 88B provide the bore 22 with diameter D2 at slots 88A and 88B that is slightly larger than diameter D1.

The slots 88A and 88B thus provide a clearance, such as for a suture anchor having a width greater than D1.

With additional reference to FIGS. 15-18, an exemplary method of using the drill guide 10 is illustrated. The drill guide 10 is arranged such that the tip 24 abuts the bone 102 at an outer surface 102a of the bone 102. To maintain the drill guide 10 in a desired position, the drill guide 10 may be arranged such that the teeth 34 grip the outer surface 102a. The drill bit 40 is inserted through the bore 22 into the bone 102 to drill a bone hole 104 through the hard, outer cortical bone layer 106 and into the relatively softer, inner cancellous bone layer 108. The bone hole 104 is concentric with the tip aperture 36 and the bore 22. The deflecting surfaces 32 center the drill bit 40 within the bore 22 to prevent possible damage to the drill bit 40 should the drill tip 44 contact the inner surface 30 of the bore 22.

Figure 17:
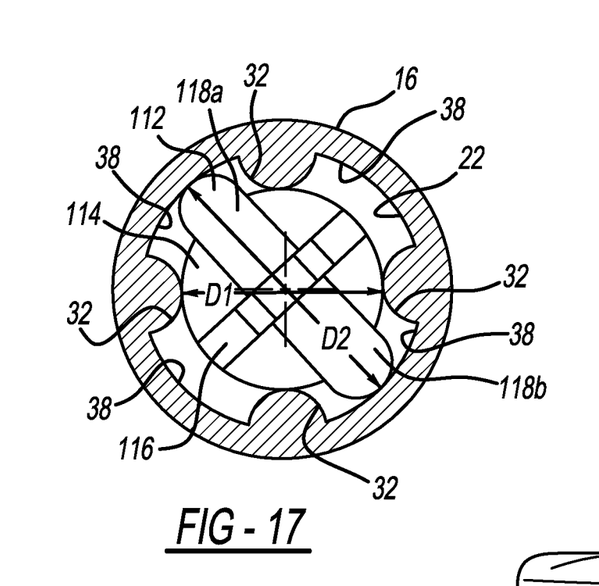
FIG. 17 is a cross-sectional view taken along line 17-17 of FIG. 16.

After the bone hole 104 has been drilled, a suitable insertion tool, such as the tool 110, with a suture anchor 112 mounted thereto is inserted into the bore 22 for implantation into the bone hole 104. Any suitable insertion tool can be used. For example, the illustrated insertion tool 110 includes an elongated, flexible shaft 114 with a hook 116 at a distal end thereof. As illustrated in FIG. 17, the shaft 114 includes a diameter D1 that is just slightly smaller than D2. Therefore, the shaft 114 closely abuts the deflecting surfaces 32 to center the insertion tool 110 within the bore 22. Because the deflecting surfaces 32 center both the drill bit 40 and the tool 110 within the bore 22, the suture anchor 112 will be aligned with the bone hole 104, thereby eliminating any need to reposition the drill guide 10 prior to implanting the suture anchor 112. Thus, once the drill guide 10 is placed in engagement with the outer surface 102a of the bone 102, both the bone hole 104 can be formed and the suture anchor 112 can be implanted without moving the drill guide 10.

The suture anchor 112 can be any suitable anchor, such as a soft, flexible anchor. As illustrated in FIG. 17, for example, the anchor 112 includes a first portion 118a and a second portion 118b that is spaced apart from the first portion 118a. The first portion 118a is connected to the second portion 118b with a suture 120, which extends through, or is connected to, the first and second portions 118a and 118b in any suitable manner.

The suture anchor 112 can be connected to the hook 116 in any suitable manner, such as by arranging the first portion 118a and the second portion 118b on opposite sides of the hook 116. As illustrated in FIG. 17, when coupled with the hook 116, the anchor 112 is generally wider than D1, the diameter between opposing centering bearings 32, but generally the same width as D2, the diameter of the bore 22 at the slots 38 of the bore 22. The slots 38 thus provide a clearance for the suture anchor 112, particularly the first and the second portions 118a and 118b, to facilitate passage of the first and the second portions 118a and 118b beyond the deflecting surfaces 32.

Figure 18:
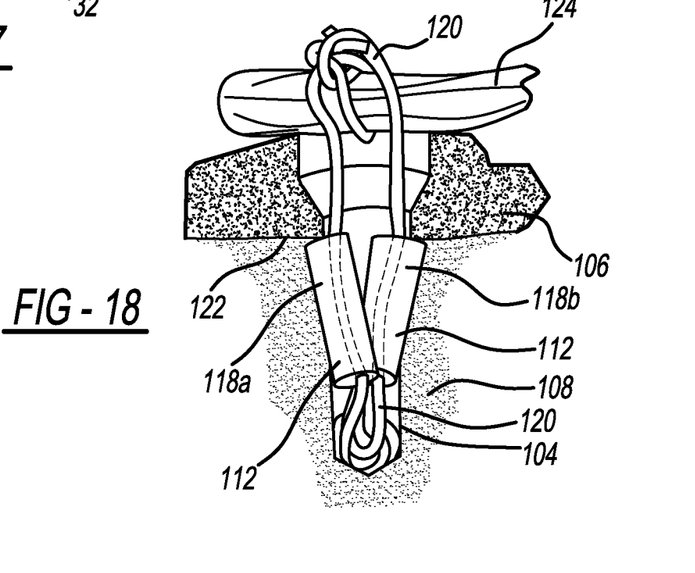
FIG. 18 illustrates the suture anchor implanted in the bone hole, tissue is held against the bone with a suture connected to the suture anchor.

With additional reference to FIG. 18, the insertion tool 110 is pushed into the bone hole 104 through the cortical bone layer 106 to position the first portions 118a and 118b within the cancellous bone layer 108. Within the bone hole 104, the first and the second portions 118a and 118b abut an undersurface 122 of the cortical bone layer 106 to retain the first and second portions 118a and 118b within the bone hole 104 to secure the anchor 112 within the bone hole 104. The anchor 112 can be used to secure any suitable material to the bone 102, such as tissue 124 to the outer surface 102a of bone 102.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A drill guide comprising:
an inner surface defining a bore extending through the drill guide, the bore configured to individually receive therein a flexible drill bit and an insertion tool with a suture anchor mounted thereto;
a tip at a distal end of the bore, the tip defining a tip aperture of the bore; and
a deflecting device that is proximal to the tip, the deflecting device including at least one deflecting surface configured to deflect the drill bit within the bore, the deflecting device defines a pair of opposing grooves configured to permit passage of a suture anchor therethrough and past the deflecting device.

2. The drill guide of claim 1, wherein:
the inner surface is curved along its length;
the deflecting surface defines a first dimension of the bore; and
a second dimension of the bore is defined between the pair of opposing grooves, the second dimension is greater than the first dimension.

3. The drill guide of claim 2, wherein the first dimension extends along a length of the curved surface proximally from the tip aperture.

4. The drill guide of claim 3, wherein the deflecting device is formed by swaging.

5. The drill guide of claim 2, wherein the deflecting device includes a first portion and a second portion that is fixedly mounted to the first portion, the second portion defines the first dimension portion and the grooves are defined within the second portion.

6. The drill guide of claim 1, wherein the deflecting surface includes a plurality of spaced apart deflecting surfaces that radially protrude from the inner surface and extend toward an axial center of the bore.

7. The drill guide of claim 1, wherein the drill guide comprises a drill guide assembly including the drill guide, the flexible drill bit, the insertion tool, and the suture anchor, the suture anchor is a soft anchor configured for implantation beyond cortical bone.

8. The drill guide of claim 1, wherein the deflecting device includes an annular ring of the inner surface that extends toward an axial center of the bore.

9. The drill guide of claim 1, wherein the drill guide is rigid and defines a side window opposite to the deflecting surface to accommodate a head of an obturator.

10. The drill guide of claim 1, further comprising:
a handle; and
an elongated linear portion extending from the handle; and
a curved portion extending from a distal end of the elongated linear portion; and
wherein the bore is further defined by each of the handle and the elongated linear portion.

11. A drill guide comprising:
a curved portion including an inner surface defining a bore extending through the curved portion, the bore configured to individually receive therein a drill bit and an insertion tool;

a tip of the curved portion at a distal end of the curved portion, the tip defining a tip aperture of the bore; and a deflection device of the inner surface that is proximal to the tip, the deflection device defining a first dimension of the bore sized and configured to deflect the drill bit and the insertion tool within the bore; and at least one groove defined by the deflection device, the at least one groove extending across the deflection device in a direction parallel to a longitudinal axis of the bore, the at least one groove configured to accommodate passage of a suture anchor mounted to the insertion tool past the deflection device;

wherein the deflection device includes a plurality of spaced apart protrusions of the inner surface that extend radially toward the longitudinal axis of the bore; and wherein the at least one groove is defined between the plurality of spaced apart protrusions.

12. The drill guide of claim 11, further comprising:

wherein the at least one groove defines a second dimension of the bore that is greater than the first dimension.

13. The drill guide of claim 12, wherein the deflection device includes an annular ring of the inner surface that extends toward a center of the bore and defines the first dimension.

14. The drill guide of claim 11, wherein the deflection device defines the first dimension of the bore along a length of the curved portion proximally from the tip aperture; and wherein the drill guide defines a side window to accommodate a head of an obturator.

15. A method of forming a bone hole in bone and implanting a suture anchor therein, the method comprising:

positioning a drill guide against an outer surface of the bone at a first location;

inserting a drill bit in a bore defined by the drill guide such that a tip of the drill bit extends out from within the bore through a tip aperture defined by the bore, the drill guide includes a deflection device with at least one deflecting surface configured to deflect the drill bit within the bore, the deflecting surface defines a first dimension of the bore;

drilling the bone hole in the bone with the drill bit; and inserting an insertion device with the suture anchor mounted thereto through the bore and implanting the suture anchor within the bone hole, the suture anchor including a width that is greater than the first dimension, the suture anchor is moved past the deflection device through grooves defined by the deflection device, the grooves define a second dimension of the bore that is greater than the first dimension.

16. The method of claim 15, further comprising securing tissue to the outer surface of the bone with a suture connected to the suture anchor.

17. The method of claim 15, further comprising moving the suture anchor through the grooves defined between a plurality of spaced apart deflecting surfaces of the insertion device.

18. The method of claim 15, further comprising moving the suture anchor through the grooves that extend generally parallel to a longitudinal axis of the bore.

19. The method of claim 15, further comprising inserting the drill bit and the insertion device with the suture anchor mounted thereto through a curved portion of the bore that extends proximally from the tip aperture toward an elongated longitudinal portion of the drill guide.

20. The method of claim 15, further comprising maintaining the drill guide at the first location while inserting the insertion device through the bore and implanting the suture anchor within the bone hole.

21. The method of claim 15, further comprising drilling the bone hole such that the bone hole is concentric with the bore at the tip aperture.

22. The method of claim 15, further comprising positioning the drill guide with an obturator seated in the bore, a head of the obturator is at a tip aperture of the drill guide, the drill guide defines a window proximate to the tip aperture to accommodate the head as the head passes over the deflecting surface.

* * * * *